United States Patent
Schulz et al.

(10) Patent No.: US 9,265,506 B2
(45) Date of Patent: Feb. 23, 2016

(54) SURGICAL INSTRUMENT

(75) Inventors: Peter Schulz, Loeffingen (DE); Markus Nesper, Tuttlingen (DE); Dieter Weisshaupt, Immendingen (DE); Konstantin Faulhaber, Frittlingen (DE)

(73) Assignee: Aesculap AG, Tuttlingen (DE)

( * ) Notice: Subject to any disclaimer, the term of this patent is extended or adjusted under 35 U.S.C. 154(b) by 1097 days.

(21) Appl. No.: 12/932,509

(22) Filed: Feb. 24, 2011

(65) Prior Publication Data

US 2011/0224654 A1 Sep. 15, 2011

(30) Foreign Application Priority Data

Mar. 12, 2010 (DE) .................. 10 2010 012 011

(51) Int. Cl.
- *A61B 17/00* (2006.01)
- *A61B 17/128* (2006.01)
- *A61B 17/16* (2006.01)

(52) U.S. Cl.
CPC ......... *A61B 17/1285* (2013.01); *A61B 17/1611* (2013.01); *A61B 17/1626* (2013.01); *A61B 17/1628* (2013.01); *A61B 2017/00548* (2013.01); *A61B 2017/00734* (2013.01)

(58) Field of Classification Search
CPC ........ A61B 17/00; A61B 17/32; A61B 17/04; B25C 1/12; B25C 1/04; B31B 1/00; B32B 45/04
USPC ............... 606/1, 169; 227/10, 19, 130, 175.3, 227/175.1, 8; 173/169; 4/255.1
See application file for complete search history.

(56) References Cited

U.S. PATENT DOCUMENTS

| | | | |
|---|---|---|---|
| 3,643,851 A * | 2/1972 | Green et al. | 227/19 |
| 3,983,947 A * | 10/1976 | Wills et al. | 173/169 |
| 4,063,317 A * | 12/1977 | Santore | 4/255.01 |
| 4,331,277 A * | 5/1982 | Green | 227/19 |
| 4,938,408 A * | 7/1990 | Bedi et al. | 227/8 |
| 4,951,861 A | 8/1990 | Schulze et al. | |
| 4,964,559 A | 10/1990 | Deniega et al. | |
| 5,018,657 A | 5/1991 | Pedlick et al. | |
| 5,364,001 A * | 11/1994 | Bryan | 227/175.1 |
| 5,397,046 A * | 3/1995 | Savage et al. | 227/175.3 |
| 6,619,529 B2 | 9/2003 | Green et al. | |
| 6,786,379 B2 * | 9/2004 | Largo | 227/10 |
| 7,431,189 B2 | 10/2008 | Shelton, IV et al. | |

(Continued)

FOREIGN PATENT DOCUMENTS

| | | |
|---|---|---|
| DE | 689 14 004 | 7/1994 |
| DE | 203 18 275 | 2/2004 |

(Continued)

*Primary Examiner* — William Thomson
*Assistant Examiner* — Victor Shapiro
(74) *Attorney, Agent, or Firm* — Lipsitz & McAllister, LLC (57) ABSTRACT

In order to further develop a surgical instrument with an energy-driven operating device, an energy storage device as well as a control device for driving the operating device as required and supplying it with energy from the energy storage device such that an optimum utilization of the capacity of the energy storage device is achieved without any risk for the surgeon or the patient, in particular in view of the different energy requirements of the individual operating processes, it is suggested that when a predetermined state of residual charge of the energy storage device is reached and/or it is fallen below for the first time the control device make its residual charge available for returning the tool into a rest position.

24 Claims, 6 Drawing Sheets

(56) References Cited

U.S. PATENT DOCUMENTS

| | | |
|---|---|---|
| 7,441,684 B2 | 10/2008 | Shelton, IV et al. |
| 7,448,525 B2 | 11/2008 | Shelton, IV et al. |
| 7,845,532 B2 * | 12/2010 | Burke et al. .................. 227/130 |
| 2006/0151567 A1 | 7/2006 | Roy |
| 2008/0029570 A1 | 2/2008 | Shelton et al. |
| 2008/0029571 A1 | 2/2008 | Shelton et al. |
| 2008/0029572 A1 | 2/2008 | Shelton et al. |
| 2008/0029573 A1 | 2/2008 | Shelton et al. |
| 2008/0029575 A1 | 2/2008 | Shelton et al. |
| 2008/0029577 A1 | 2/2008 | Shelton et al. |
| 2008/0251569 A1 * | 10/2008 | Smith et al. ................. 227/175.1 |
| 2008/0300580 A1 * | 12/2008 | Shelton et al. ..................... 606/1 |
| 2009/0209990 A1 * | 8/2009 | Yates et al. .................... 606/169 |

FOREIGN PATENT DOCUMENTS

| | | |
|---|---|---|
| DE | 20 2007 006 801 | 8/2007 |
| DE | 20 2010 003 854 | 10/2010 |
| EP | 1 884 205 | 2/2008 |
| WO | WO 2009/109198 | 9/2009 |

* cited by examiner

SURGICAL INSTRUMENT

This application claims the benefit of German Patent Application No. 10 2010 012 011.1 filed on Mar. 12, 2010.

The present disclosure relates to the subject matter disclosed in German application number 10 2010 012 011.1 of Mar. 12, 2010, which is incorporated herein by reference in its entirety and for all purposes.

BACKGROUND OF THE INVENTION

The invention relates to a surgical instrument with an energy-driven operating device, an energy storage device as well as a control device for operating the operating device as required and supplying it with energy from the energy storage device.

Instruments of this type are known with an operating device which is driven electrically or pneumatically. Accumulators or batteries or rather gas cartridges serve as energy storage devices.

The energy capacity is necessarily limited in the case of such instruments, with the risk that operating processes can no longer be finished when the charge capacity is exhausted. This is a problem, in particular, in the case of operations which relate to the central nervous system when the instruments are used to remove, for example, bones or tissue material from the patient with a considerable use of force, for example with so-called bone punches.

In the case of bone punches, forces of approximately 700 to approximately 750 N occur when bone material is removed. If the supply of energy fails while a punch cutter is being transferred from an operating position into an end position, in which the operating process is brought to an end, it remains on the bone and can become locked in position. The problem for the surgeon is then that the bone punch cannot be released from the patient and replaced by another instrument ready for use.

Other fields of use relate to clip appliers for, for example, vessel clips, anastomosis clips as well as aneurysm clips. Furthermore, the fields of use relate to so-called rongeurs or also other cutting instruments which must reliably remove body tissue or bone material in a manner similar to the punches specified above.

It is important for all these fields of use that an operating cycle can be run through such that, afterwards, the instrument is again in a defined starting position or rest position.

On the other hand, it is of significance in the case of the surgical instruments of the present invention that size and weight of the instrument are balanced with a view to ergonomic aspects. The space for accommodating the energy storage device is considerably restricted as a result. A generous dimensioning of the energy storage device from the point of view of safety cannot be realized for this reason alone. A permanent connection to an external energy source is also not desirable from an ergonomic point of view.

In many cases, operations do, however, require a supply of energy which would necessitate too large a volume and weight for one single energy storage device. This situation, in which the energy storage device is exhausted during an operation once or several times, is, therefore, foreseeable in many cases. In such a case, care has to be taken for the reasons specified that the instrument does not remain in an undefined operating state when the energy storage device is exhausted since this would entail a risk for the patient being treated and, in addition, hinder the work of the surgeon.

It has so far been suggested in the state of the art to dimension the energy storage device as far as possible such that all the operating processes can be completely finished with the charge capacity available. This can be brought about in the case of so-called clip appliers relatively simply in that the capacity of the clip magazine is reduced so that all the clips in the magazine can be applied before the energy storage device is exhausted.

In the case of instruments, with which the energy requirements per operating step cannot be predetermined so easily and precisely, it has been suggested in EP 1 884 204 A2 to use a counter for monitoring the supply of energy and to stop use of the instrument when it is likely from the number of operating processes that the energy storage device is almost exhausted.

Operation without any risk can be realized with this manner of proceeding only when the number of permissible operating processes is selected such that use of the instrument is stopped long before exhaustion of the energy storage device is reached.

A similar measure is also suggested in U.S. Pat. No. 6,619,529 B1 for a surgical clip applier, with which a counter likewise records the operating processes and use of the instrument is stopped after a predetermined number of operating processes, i.e. clips applied.

These concepts are unsatisfactory, in particular, for instruments which are more complex from an energy point of view since the supply of energy from the energy storage device can be used only very incompletely on account of the different energy requirements per operating process or, in another case, the risk is still present of the instrument no longer being supplied with the necessary energy while an operating process is being carried out, with the consequences described above.

The object of the present invention is to further develop a surgical instrument of the type described at the outset such that an optimum utilization of the capacity of the energy storage device is achieved without any risk for the surgeon or the patient, in particular in view of the different energy requirements of the individual operating processes.

SUMMARY OF THE INVENTION

This object is accomplished by an instrument in accordance with claim 1.

On account of the control device used in accordance with the invention, the capacity of the energy storage device can be used individually depending on the energy requirements of the individual operating processes and when a predetermined state of residual charge is reached and/or this is fallen below for the first time, the residual charge of the energy storage device is available for returning the tool into a rest position.

In this way, a better exploitation of the energy stored in the energy storage device may be realized in the case of clip appliers, for example appliers for vessel clips, anastomosis clips, aneurysm clips etc.

The control device of the instrument according to the invention preferably comprises a monitoring unit which detects the actual state of charge of the energy storage device and blocks any renewed activation of the tool when the predetermined state of residual charge is reached and/or it is fallen below for the first time.

The predetermined state of residual charge is preferably selected such that the last operating process initiated can be safely finished. The operating cycle must not, therefore, be interrupted prematurely in order to be able to transfer the tool of the operating device into an end position and back again.

If the mode of operation of the operating device necessitates a transfer of the tool from a rest position into an end position and back which requires a lot of energy, there is still an adequate supply of energy remaining for the transfer of the tool of the operating device back into the rest position. If the surgeon has possibly not completed all his work, the instrument can be exchanged or provided with a charged energy storage device.

This is the case, in particular, for cutting and punching instruments, such as, for example, rongeurs, bone punches etc. In this case, as well, an improved exploitation of the supply of energy in the energy storage device is achieved in comparison with a rigidly predetermined number of operating processes.

In this case, it may also be of advantage when the predetermined state of residual charge can be adjusted. The use of the supply of energy can thus be coordinated more exactly with the energy consumption of the respective operating steps to be carried out.

The instrument according to the invention preferably has an indicator unit, in particular as part of the control device, which indicates the state of charge of the energy storage device. This can comprise an indicator function which shows that the predetermined state of residual charge has been reached and/or it is fallen below for the first time and so the surgeon not only recognizes the lack of functioning or the blocking of the operating device but information is indicated to him, in addition, concerning the reason for the blocking.

The energy storage device will then be exchanged or fully charged again. Once the energy storage device has been exchanged or charged, the indicator unit will be reset again to the normal operating state.

This indicator function can be configured in an optical and/or tactile manner.

In the case of preferred instruments, the indicator unit can make the actual state of charge apparent and so during operating with the instrument the state of charge can be followed and, for example, the imminent blocking of the operating device recognized beforehand. Where applicable, the reaching and/or falling below for the first time of the predetermined state of residual charge will be indicated, in addition, with an additional indicator element.

The instruments according to the invention often have a handle which can be advantageously used in many cases for accommodating the energy storage device.

The energy storage device is preferably connected to the instrument so as to be exchangeable so that the used energy storage device can be exchanged for a fresh one when the predetermined state of residual charge is reached and/or it is fallen below.

The energy storage device is preferably an energy storage device which can be charged and, where applicable, exchanged.

It may also be provided for the instrument to be accommodated in a charging station as a whole, together with the energy storage device, for the purpose of charging the energy storage device.

If gas cartridges are used as energy storage devices, it may be provided for the monitoring unit to comprise a pneumatically actuatable valve which allows activation of the operating device and, where applicable, transfer of the operating device from the rest position into the operating position or end position as long as the state of charge of the gas cartridge is above the predetermined state of residual charge. When the state of residual charge is reached and/or it is fallen below for the first time, the functioning for the transfer of the operating device from the operating position or end position into the rest position remains available, wherein the residual energy of the energy storage device will be used for this purpose.

In an alternative embodiment of the invention it is provided for the energy storage device of the instrument to comprise a first and a second storage element, wherein the monitoring unit makes the second storage element available for the transfer of the operating device from the operating or end position back into the rest position when the predetermined state of residual charge of the first storage element is reached and/or it is fallen below for the first time.

A small, second storage element is adequate for this purpose since energy need be kept only for the last partial step of an operating process. The main storage device in the form of the first storage element then supplies the energy for all the preceding operating processes. A spring compressed during the operating process can also serve as a small, second storage element.

In the case of the bone punch, the monitoring of the state of charge of the first storage element is then sufficient since it can safely be assumed that an adequate amount of energy will still be available in the other storage element for returning the operating device into the rest position following the last possible operating process.

Alternatively, a second storage element of the same size or larger can be provided in one preferred instrument and so the first storage element serves to transfer the operating device from the rest position into the operating and end position and the second storage element serves to transfer the operating device back into the rest position. This lends itself, in particular, for the supply of energy to bone punches since the energy requirements for the transfer of the operating device into the operating and end position necessitate more energy than the return movement from the end position into the rest position.

The second storage element preferably has an energy content which is greater than approximately 105%, in particular approximately 110%, of the energy which is required at the most for the required number of return movements. Typically, a pneumatic cylinder which is of larger dimensions will be provided for the advancing of the tool into the operating and/or end position than for the return of the tool into the rest position.

In a further, preferred embodiment, both storage elements are connected to form a unit so that both storage elements must, of necessity, always be replaced together. At the same time, the exchange can be carried out with one single procedure.

The invention relates, in addition, to a method for operating an energy-driven surgical instrument according to claim 12.

Advantageous developments of this method are the subject matter of claims 13 to 16.

These and other advantages of the invention will be explained in greater detail in the following on the basis of the drawings.

DETAILED DESCRIPTION OF THE INVENTION

Figure 1:
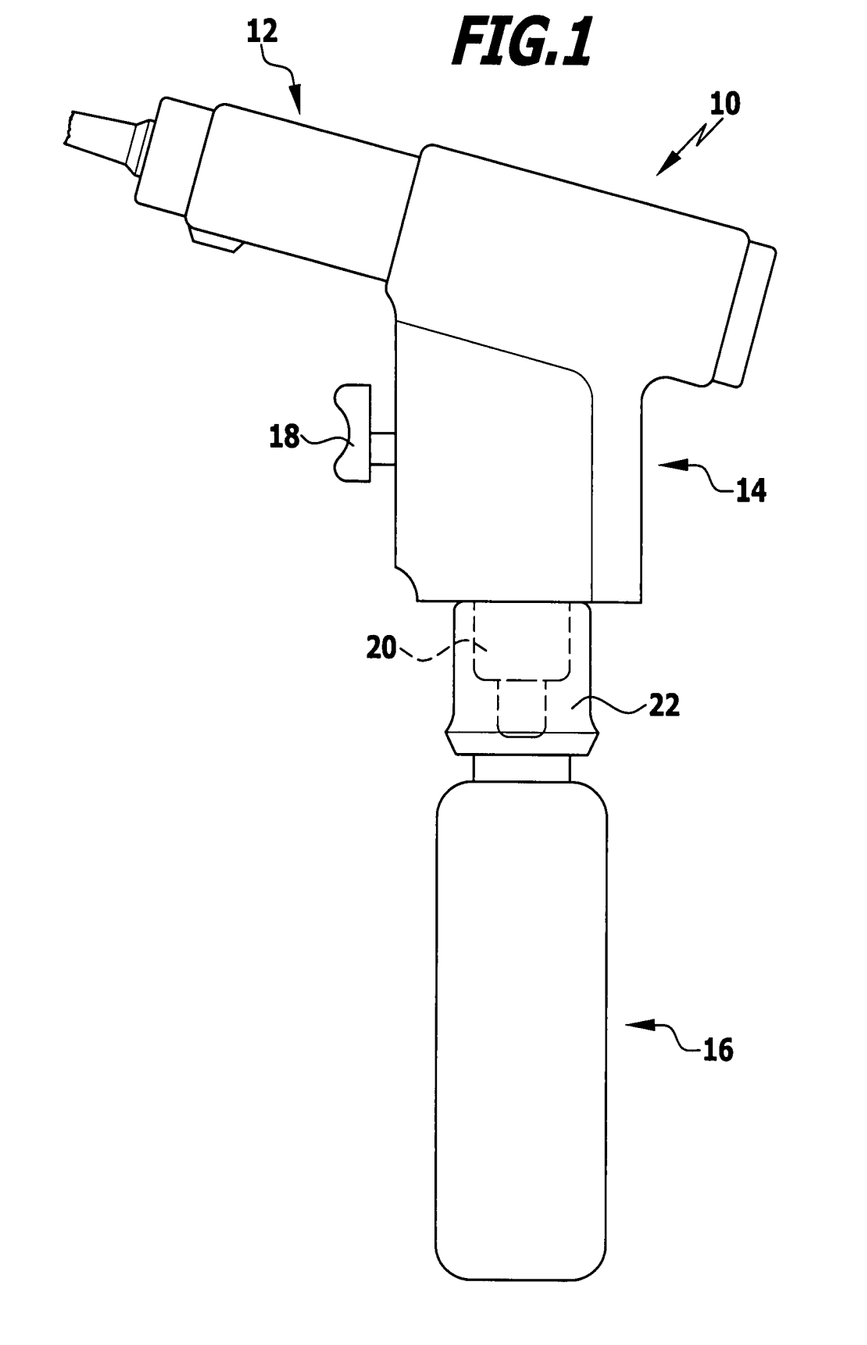
FIG. 1 shows an instrument according to the invention in the form of a pneumatically driven clip applier.

FIG. 1 shows an instrument according to the invention in the form of a pneumatically driven clip applier 10 with an operating device 12 (shown only partially) designed as an applier, a handle 14 as well as an energy storage device in the form of a gas cartridge 16.

The clip applier 10 comprises a compressed gas drive (not shown) which is arranged in its handle 14 and actuates the applier mechanism. The clip applier 10 is controlled via a push-button switch 18 which projects out of the handle 14 which is preferably in the shape of a pistol.

A connection flange 20 which can be releasably connected to the gas cartridge 16 protrudes at the lower end of the handle 14. For the connection to the handle 14, the gas cartridge 16 has a short connection piece 22, with which the gas cartridge 16 can be connected to the connection flange 20 of the handle in a gas-tight manner.

With respect to the details of the gas-tight connection between handle 14 and gas cartridge 16, attention may be drawn to DE 203 18 275 U1, to the content of which reference is made in full in this connection.

Figure 2:
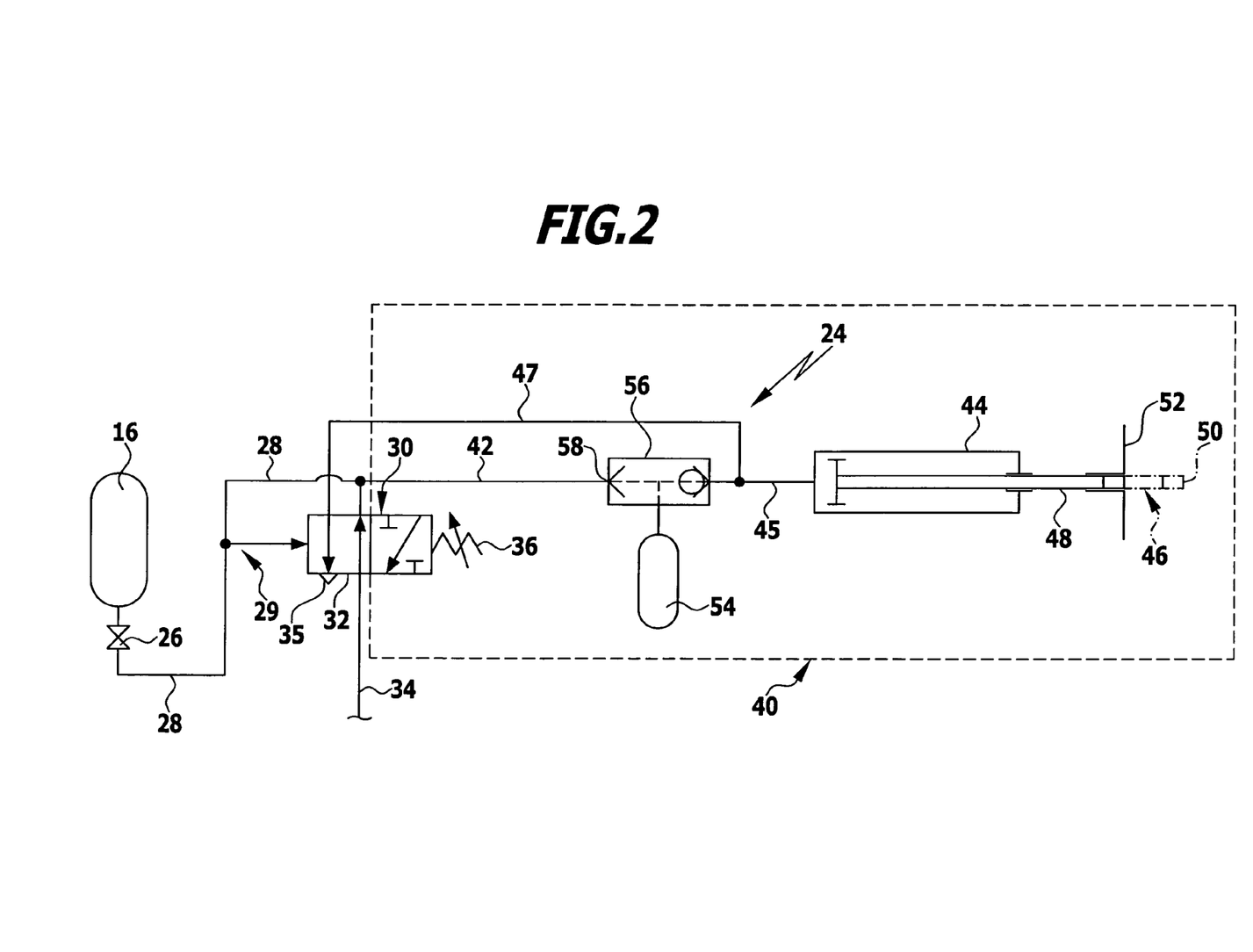
FIG. 2 shows a schematic circuit diagram of a first control of an instrument according to the invention in accordance with FIG. 1.

The clip applier 10 according to the invention is characterized by a control device 24, as is apparent by way of example from the circuit diagram of FIG. 2.

The control device 24 is connected to the gas cartridge 16, which has, for example, a tank filled with $CO_2$ at a pressure of approximately 60 bar, via an adapter interface 26 (connection flange 20 and short connection piece 22).

A supply line 28 leading from the adapter interface 26 to the control device 24 is connected via a branch 29 to a monitoring unit 30 which provides a connection to the operating pressure line 34 of the applier 10 by means of a switching element 32 when the gas pressure in the supply line 28 is sufficient for the actuation of the clip applier 10.

The switching element 32 is shown in FIG. 2 in a first operating position, in which the gas pressure which acts via the branch 29 is sufficient to neutralize the adjustable pressure force of a spring 36. If the gas pressure in the supply line 28 drops to or for the first time below a predetermined threshold pressure which corresponds to a state of residual charge of the gas cartridge 16, the switching element 32 will be displaced by the spring 36 from its position shown in FIG. 2 into a second position, in which the connection of the operating pressure line 34 to the supply line 28 is interrupted. At the same time, the supply line 28 will be connected to a venting opening 35 of the switching element 32 and the cartridge 16 made pressure-less. As a result, the activation of the instrument is blocked.

The threshold value of the state of residual charge is set, for example, by means of the pretensionable spring 36 such that a reliable functioning of the clip applier 10 is provided until this pressure is reached and also when it is fallen below for the first time, i.e. an adequate closing pressure can still be applied for the clip last applied.

The return movement of the applier 10 can be brought about, for example, by a spring of the operating device 12 which is pretensioned during the application process since, for this purpose, no particularly high forces are required. This spring then undertakes the function of a second energy storage element.

The state of reaching or falling below the predetermined state of residual charge will preferably be made apparent to the user by means of an indicator unit 40 which can be of very different designs.

In the embodiment of FIG. 2, the monitoring unit 30 is equipped with an additional switching function which forms part of the indicator unit 40. The indicator unit 40 is connected to the supply line 28 of the energy storage device 16 via a control line 42.

The indicator unit 40 has an indicator element 44 with a pneumatically extendable warning indication plunger 46. If the pressure in the supply line 28 drops to that of the state of residual charge of the gas cartridge 16, the plunger 46 will be moved out of its rest position 48 into an indication position 50 (position illustrated by dash dot lines), in which it projects beyond the surface 52 of the handle 14, as will be explained in the following. As a result, a signal which can be discerned sensorially (haptically) in the best possible manner will be given to the user of the instrument.

First of all, however, a separate pressure storage device 54, which is connected to the control line 42 via a changeover valve 56, will be filled with the initial pressure of the energy storage device 16 present in the control line 42. If the pressure in the control line 42 drops and the spring 36 presses the monitoring unit 30 into its second switching position, the supply line 28 and also the control line 42 will be vented. As a result, the energy storage device 16 will be vented at the same time, as described above. A line 47 previously vented via the monitoring unit 30 will now be closed by the monitoring unit 30. In the pressure-less state on the input side 58, the changeover valve 56 will switch the separate pressure storage device 54 to a line 45 which connects the changeover valve to the line 47 and the indicator element 44. Since the line 47 is blocked, the pressure of the separate pressure storage device 54 will become effective in the indicator unit 44 and convey the indicator plunger 46 out of the rest position 48 into the extended indication position 50.

The indication that the threshold value for the energy storage device 16 has been reached or it is fallen below will occur suddenly and in a very perceptible manner.

Alternatively (not shown), the pressure of the energy storage device is allowed to act on a spring which presses the warning plunger into the indication position. If the operating pressure is sufficient, the warning plunger remains in the retracted, hidden position; if the pressure drops below the threshold value, the pressure chamber of the warning plunger will be vented and the spring presses the warning plunger momentarily into the indication position.

In accordance with a further alternative (not shown), the warning plunger travels out of the rest position into the indication position proportionally to the decreasing operating pressure.

In accordance with a further alternative (not shown), the warning plunger is pressed successively out of the indication position into the rest position when the pressure of the energy storage device decreases.

Figure 3:
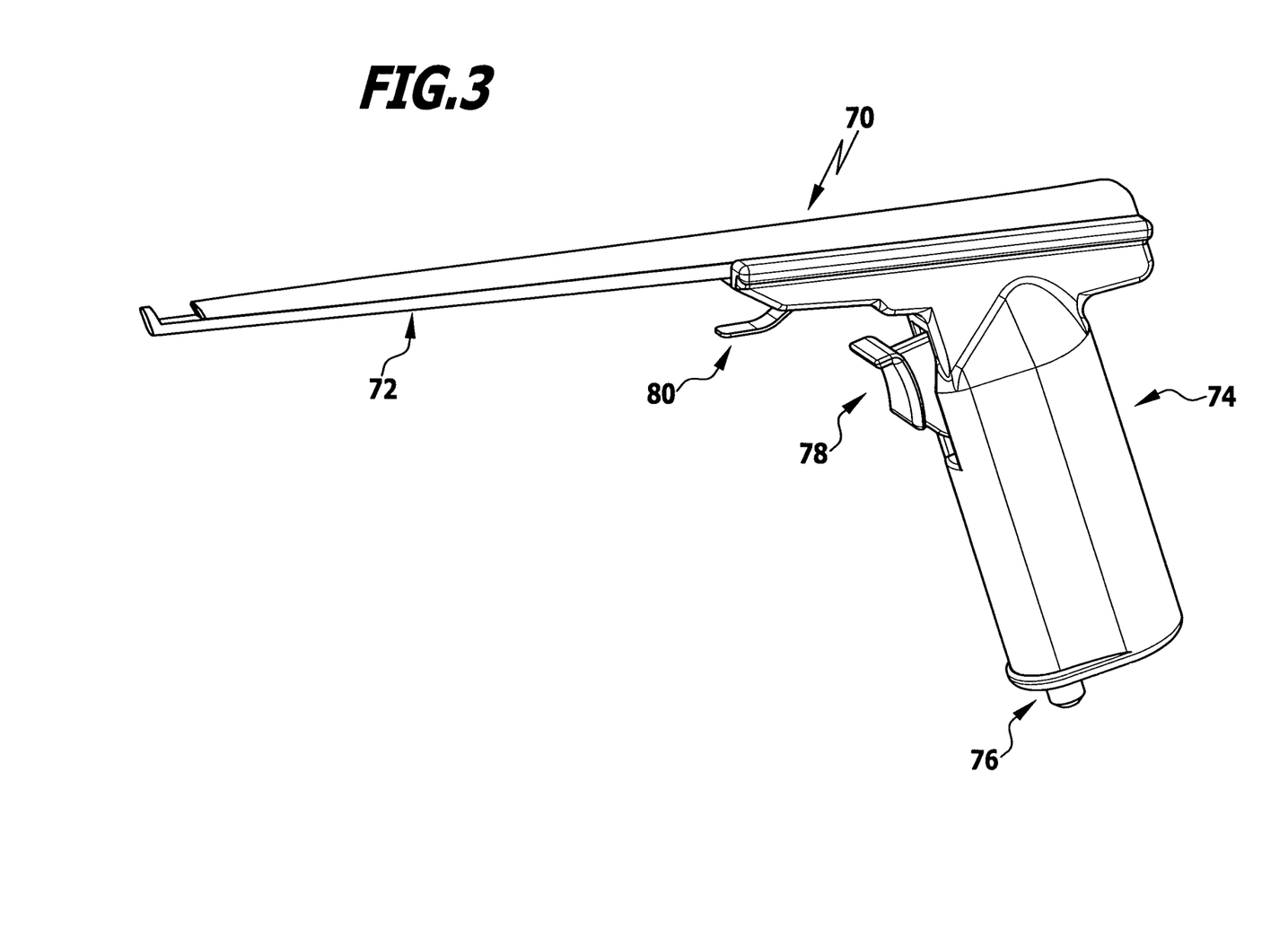
FIG. 3 shows an instrument according to the invention in the form of a pneumatic bone punch.

FIG. 3 shows an instrument which is designated with the reference numeral 70 and is in the form of a bone punch with an operating device 72 and a handle 74. The handle 74 has a short connection piece 76, by means of which an energy storage device, in particular a gas pressure cartridge, can be releasably connected to the bone punch 70.

The bone punch may be actuated via a push-button switch 78. An operating process initiated via the push-button switch 78 comprises the advancing movement of a punching tool out of a rest position in the direction towards a counter bearing (details not shown), between which the tissue or bone material to be removed is arranged. Once the tool has reached its end position and has severed the tissue or bone material, a further operating process will be triggered, in which the tool is returned from the end position into its rest position.

This process requires a lot of energy, in part, since the tool can become stuck in the tissue or bone material. As a result, it is important for the reliable functioning of the bone punch that sufficient energy is available for this operating process since, otherwise, there is the risk of it remaining bonded to tissue or bone material in a force locking manner.

Figure 4:
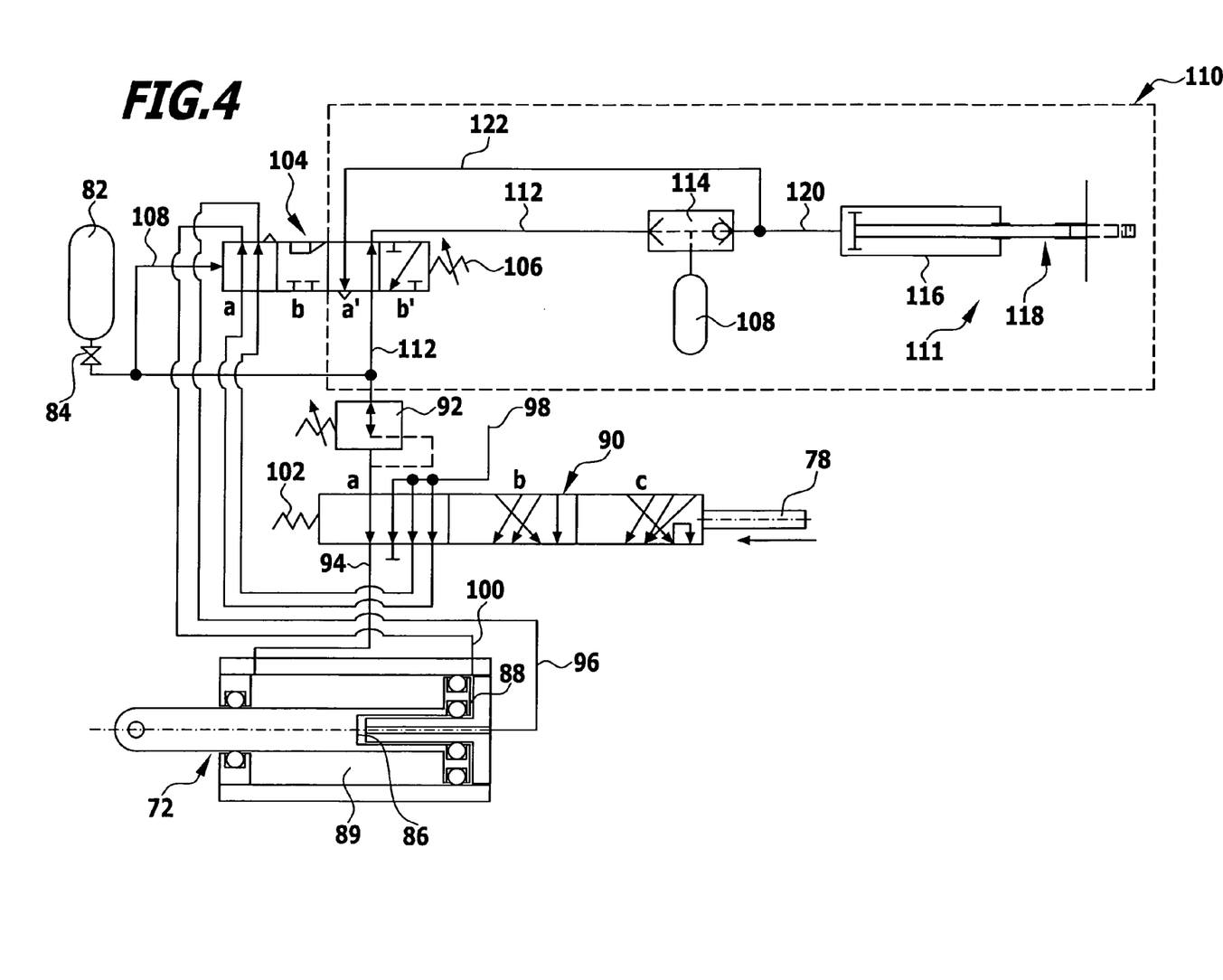
FIG. 4 shows a schematic circuit diagram of a control for the instrument according to the invention in accordance with FIG. 3.

FIG. 4 shows a first embodiment of a circuit diagram for the instrument 70 according to the invention and shown in FIG. 3. A tank 82, for example a $CO_2$ cartridge with a filling pressure of 60 bar, serves as energy storage device. The tank 82 is connected releasably to the connection 76 of the handle 74 via an adapter interface 84.

The schematically illustrated operating device 72 with a punching tool has a first cylinder 86, with which the punching tool can be transferred from the rest position into an operating position. A second cylinder 88 makes the continuation of the movement of the punching tool possible from the operating position into an end position, if necessary with increased force. A return of the punching tool of the operating device 72 into the rest position is brought about by means of a third cylinder 89. Since greater forces are generally required for the return movement, the operative surface of the third cylinder 89 is selected to be larger than that of the first cylinder 86.

A first control valve 90 is actuated via the push-button switch 78 and this has three switching positions.

In a first switching position a (as shown in FIG. 4), the control valve 90 connects the energy source (tank 82), which is optionally connected via a regulator 92, to a supply line 94 which is connected, on the other hand, to the third cylinder 89. In this state, the compressed gas keeps the punching tool in its rest position.

A supply line 96 to the first cylinder 86 of the operating device 72 is connected to a venting opening 98 in this state. A supply line 100 to the second cylinder 88 is likewise connected to the venting opening 98 and so the return movement of the cylinder during the transfer of the punching tool into the rest position can take place without any appreciable counterpressure.

If the push-button switch 78 is actuated, the first control valve 90 reaches, first of all, a second switching position b, in which the compressed gas drawn from the regulator 92 passes into the first cylinder 86 via the supply line 96 and moves the punching tool in the direction of the operating position. At the same time, the supply line 100 is connected to the venting opening 98 and vents the chamber of the second cylinder 88. The supply line 94 is likewise connected to the venting opening 98 and so the advancing movement in the direction of the operating position can take place essentially without any counterpressure.

If the push-button switch 78 is pushed right in, the first control valve 90 moves into its third switching position c, in which the supply line 100 and, therefore, the second cylinder 88 are also supplied with compressed gas from the tank 82 so that the punching process can be reliably brought to a conclusion. In this respect, the punching tool passes from the operating position into the end position. Tissue or bone material is thereby severed.

Afterwards, the surgeon will release the push-button switch 78 and the first control valve 90 returns to the first switching position a on account of the spring force of the spring 102. The third cylinder 89 will be acted upon with compressed gas via the supply line 94 whereas the supply lines 96, 100 are connected to the venting opening 98. The return movement of the punching tool of the operating device 72 is, therefore, brought about practically without any counterpressure.

The supply lines 96 and 100 are, in accordance with the invention, not supplied directly with the compressed gas drawn from the regulator 92 but rather they can be interrupted via a second control valve 104 which engages in the supply lines. FIG. 4 shows the second control valve 104 in its first switching position a, in which it releases the supply lines 96, 100. The second control valve 104 is held in its first switching position a contrary to the spring force of a spring 106 by the pressure force of the gas supply in the tank 82 which acts via a line 108.

If the pressure in the tank 82 drops below a predetermined threshold value (state of residual charge), the spring 106 presses the second control valve 104 into its second switching position b, in which the supply lines 96, 100 coming from the first control valve 90 are interrupted and end blindly in the second control valve 104 while their sections on the side of the punching tool are short-circuited with one another and vented. A supply of the punching tool with compressed gas is no longer possible in this switching position b, i.e., a renewed activation of the tool of the operating device is blocked.

In order to make the surgeon aware of the operating state of the instrument and in order to indicate the fact that the energy storage device needs to be changed, the instrument is preferably equipped with an indicator unit 110 for the state of charge of the energy storage device. For this purpose, the second control valve 104 preferably has a second function, the two switching states a' and b' of which are shown in the right-hand half of the second control valve 104.

In the first switching position of the second control valve 104 a and a', respectively, during which the instrument can be actuated as usual, a small pressure storage device 108 for an indicator device 111 is filled with compressed gas of the tank 82 by means of a supply line 112. The pressure storage device 108 is connected to the supply line 112 by a changeover valve 114. An adjusting cylinder 116 for an indicator element 118 (e.g., in the form of a pin) of the indicator device 111 is connected via a line 120 to an additional connection of the changeover valve 114. During the regular operation of the instrument, i.e. as long as the pressure in the tank 82 is sufficient to keep the second control valve 104 in its switching position a and a', respectively, this line 120 is connected to a venting opening via a line 122, which likewise leads to the second control valve 104, and it is, therefore, without pressure.

If the pressure of the compressed gas prevailing in the tank 82 drops below a threshold value, the second control valve 104 will be transferred into its second switching position b and b', respectively, by means of the spring force of the spring 106. In this switching position b', the supply line 112 is interrupted from the side of the regulator 92. At the same time, the part of the supply line 112 which leads to the pressure storage device 108 will be vented on the side of the second control valve 104. The line 122 is blocked at the control valve 104. In this situation, the changeover valve 114 switches over so that the pressure of the pressure storage device 108 now acts on the adjusting cylinder 116 of the indicator device 111 and the indicator element 118 travels out of its rest position into its indication position (in FIG. 4 the position shown by dashed lines). The information concerning the blocked drive of the punching tool is thus transmitted to the surgeon working with the instrument sensorially and so he can replace the energy storage device (tank 82).

The punching tool of the operating device 72 can still be brought reliably into its starting position in this state, as described above, and so the instrument can be removed from the field of operation without any problem.

Figure 5:
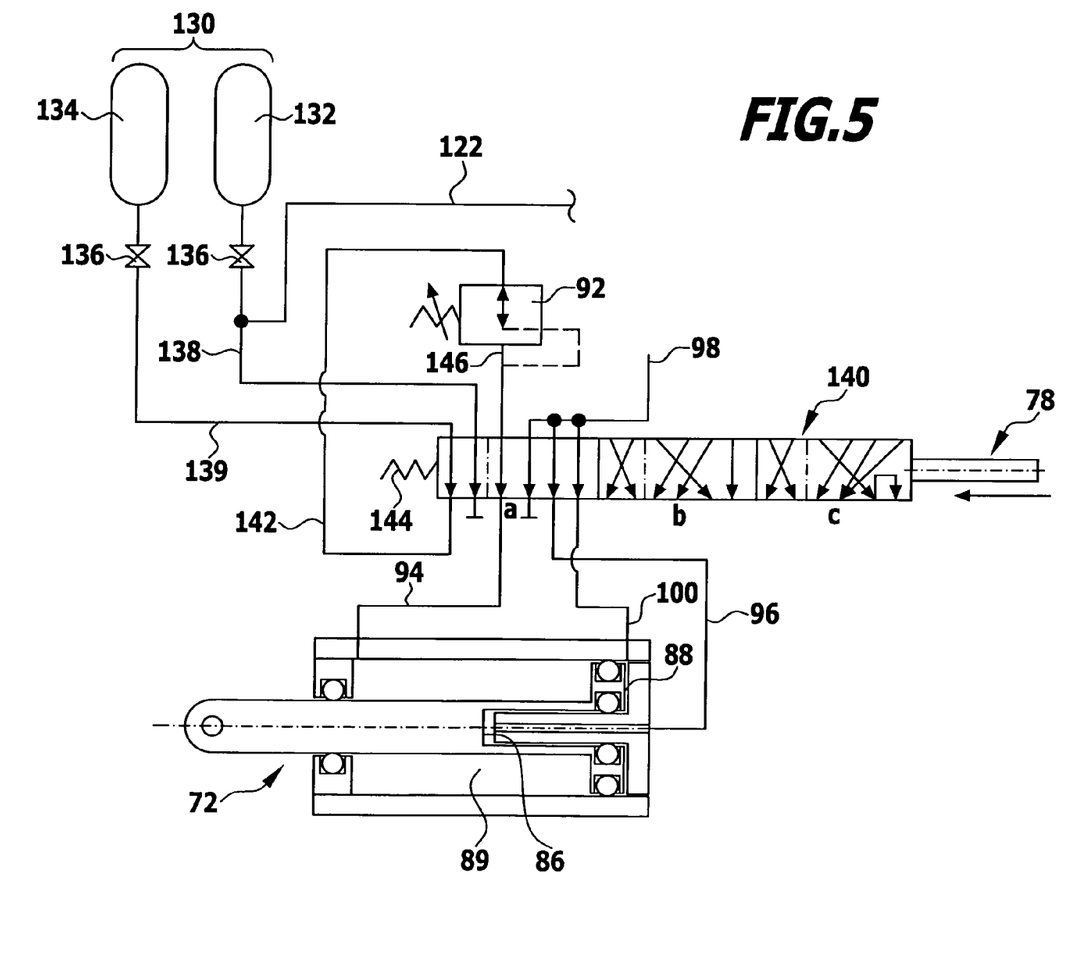
FIG. 5 shows a schematic circuit diagram of an alternative control for the instrument according to the invention in accordance with FIG. 3.

Another configuration of the instrument according to the invention in FIG. 3 is shown in FIG. 5. Instead of the single tank 82, a double tank 130 is used in this case, the one chamber 132 of which is used for the advancing movement of the punching tool of the operating device 72 and the other chamber 134 of which is used for the return movement of the punching tool into the rest position.

The control functions are, in part, similar to those of the embodiment of FIG. 4 and so the same reference numerals have been used for the same parts.

This control of FIG. 5 differs with respect to its functioning from that described previously, in principle, in that a renewed activation of the tool of the operating device 72 will not be blocked when the state of residual charge of the energy storage device drops to or below a predetermined threshold value but rather two separate energy storage modules are used: one module for the operating phase (tool is moved out of the rest position into the operating position and subsequently into the end position), the other module during the return movement of the tool into the rest position. The two energy storage modules can, by all means, advantageously form one constructional unit.

Since the operating phase typically requires a somewhat greater energy consumption than the return movement of the tool, for example approximately 10%, it is ensured with the same dimensioning of the storage capacity of the modules that the tool can be returned to the rest position after every operating phase. Even if the supply of energy during an operating phase should start to run low, it is guaranteed that the tool can be returned to the rest position again. Only the last operating step would need to be repeated once the energy storage device has been changed.

In detail, the one energy storage module in the form of the pressure chamber 132 is releasably connected to the handle 74 of the instrument via an adapter interface 136. This also applies for the other module, the pressure chamber 134.

Supply lines 138 and 139, respectively, lead from the pressure chambers 132, 134 to a control valve 140, from there a supply line 142 leads to the pressure regulator 92 which is connected to the control valve 140 with a supply line 146 and, finally, can be optionally connected to the three cylinders 86, 88, 89 by means of the supply lines 94, 96, 100.

In the non-actuated state of the push-button switch 78, the control valve 140 is held in the switching position a shown in FIG. 5 by means of the spring force of the spring 144.

In this switching position a, the supply line 138 is blocked by the control valve 140 while the supply line 139 coming from the pressure chamber 134 is switched through to the supply line 142. Since the pressure chamber 134 serves the purpose of returning the tool into the rest position, the line 146 is connected to the supply line 94 in the switching position a and acts on the third cylinder 89 with compressed gas.

The supply lines 96 and 100 of the first and second cylinders 86, 88 are connected to the venting device 98 via the control valve 140 and so the return movement of the tool into the rest position can essentially take place without any counterpressure.

If the push-button switch 78 is actuated and the control valve transferred into the switching position b, the supply line 139 is blocked while the supply line of the pressure chamber 132 is connected via the regulator 92 to the supply line 96 and, therefore, to the first cylinder 86. The compressed gas of the pressure chamber 132 which is fed into the first cylinder 96 moves the tool of the operating device 72 out of the rest position into an operating position while the third cylinder 89 is vented and the second cylinder 88 is ventilated.

The switching position c of the control valve 140 will not become active until the push-button switch 78 is pressed in entirely. In this case, the third cylinder 89 remains vented while the second cylinder 88 is acted upon, in addition, with compressed gas and so the tool of the operating device 72 is moved into the end position with the pressure prevailing in the first and second cylinders 86, 88 and the operating step can be finished. When the push-button switch 78 is released, the control valve 140 is moved back into the switching position a with the force of a spring and the supply of compressed gas described at the outset will start to return the tool into the rest position.

In order to inform the surgeon about the state of charge of the energy storage device or keep him informed, it may be provided for the state of charge of the pressure chamber 132 to be made visible and, in particular, also tangible via an indicator unit. The supply line 122 shown in FIG. 5, which branches off the supply line 138 of the pressure chamber 132, can serve this purpose.

One example for this has already been explained in conjunction with the embodiment of the invention according to FIG. 4. Further examples for an indicator unit for instruments according to the invention will be described in conjunction with FIGS. 6A and 6B.

Figure 6A:
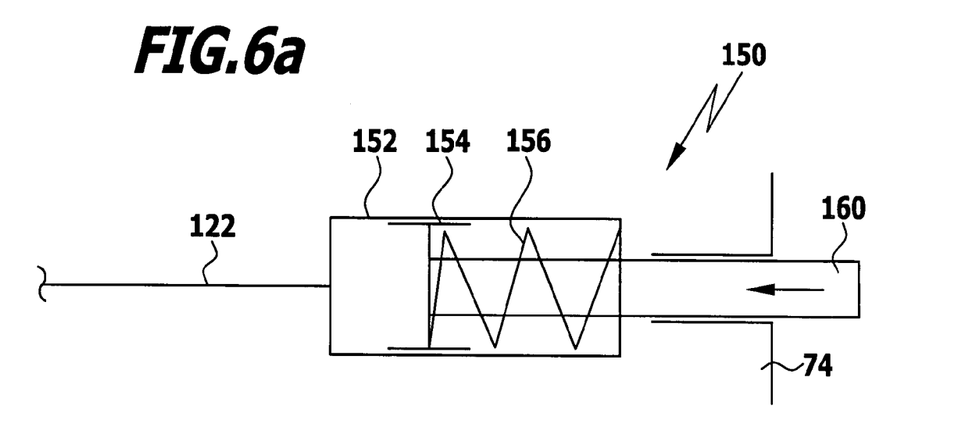
FIGS. 6A and 6B show two variations of an indicator unit for an instrument according to the invention.

FIG. 6A shows an indicator unit 150 which is connected to the supply line 122 coming from the pressure chamber 132. The pressure of the pressure chamber acts on a cylinder 152, in which a piston 154 is mounted for longitudinal displacement.

The gas pressure prevailing in the supply line 122 or rather in the cylinder 152 moves the piston 154 contrary to the force of a spring 156 to the right in FIG. 6A so that an indicator element 160, which is mounted on the piston 154 and is, for example, in the shape of a pin, travels out of the housing of the handle 74 with its free end proportionally to the gas pressure. If the gas pressure decreases, the spring 156 presses the indicator element 160 successively back into the retracted initial position, in which the free end of the pin is accommodated in the handle 74. The state of charge of the pressure chamber 132 may, therefore, be read from the position of the extended pin. The pin may also be provided with markings (not shown) for better judging the state of charge.

Figure 6B:
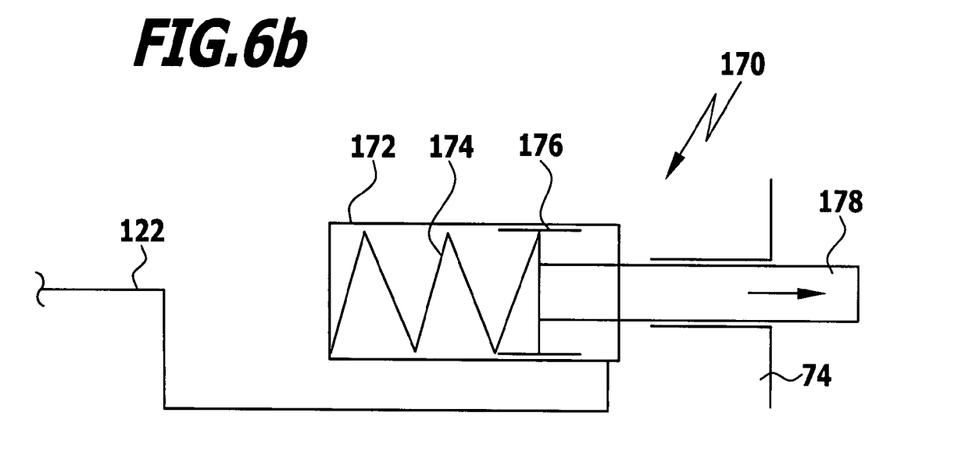

FIG. 6B shows an alternative embodiment of an indicator unit 170 which is likewise connected to the supply line 122. The indicator unit comprises a cylinder 172, in which a piston 176 loaded with a spring 174 is arranged. A pin-like indicator element 178 is mounted on the piston 176 and its free end can travel out beyond the surface of the handle 74.

If the gas pressure in the pressure chamber is high, the force of the pressure is sufficient to press the piston to the left in FIG. 6B contrary to the action of the spring 174 so that the free end of the indicator element 178 is essentially flush with the surface of the handle. The spring 174 presses the indicator element out of its first position proportionally to the decreasing gas pressure and the free end of the pin projects ever more beyond the surface of the handle 74, the lower the pressure in the pressure chamber 132.

In this case, as well, markings (not shown) on the pin of the indicator element are recommended so that it is apparent when the pressure in the pressure chamber is insufficient for any further operation with the instrument.

In general, it is to be noted that the embodiments described in the above can, of course, be converted by the person skilled in the art such that electrical energy storage devices replace the gas pressure storage devices. The person skilled in the art will then replace the pneumatic circuits described by corresponding electrical ones with the same function.

The invention claimed is:
1. Surgical instrument, comprising:
an energy-driven operating device,
an energy storage device, and
a control device for supplying the operating device with energy from the energy storage device, wherein
the operating device comprises a tool, the tool having an end or operating position and a rest position,
the control device supplies the operating device with energy as required for operating the tool,
when a state of charge of the energy storage device has either reached a predetermined state of a residual charge or has fallen below the predetermined state of the residual charge for a first time, the control device makes the residual charge available for returning the tool into the rest position,
the energy storage device comprises a gas cartridge,
the control device comprises a monitoring unit for detecting the state of charge of the energy storage device,
the monitoring unit comprises a pneumatically actuatable valve allowing activation of the tool of the operating device and, where applicable, a transfer of the tool of the operating device from the rest position into the end or operating position as long as the state of charge of the gas cartridge is above the predetermined state of residual charge.
2. Instrument as defined in claim 1, wherein the monitoring unit blocks any renewed activation of the tool of the operating device when the state of charge has reached the predetermined state of residual charge or has fallen below the predetermined state of residual charge for the first time.
3. Instrument as defined in claim 1, wherein the predetermined state of residual charge is adjustable.
4. Instrument as defined in claim 3, wherein the predetermined state of residual charge is adjustable such that the tool of the operating device is adapted to be transferred from the end or operating position into the rest position after the activation of the tool has been blocked.
5. Instrument as defined in claim 3, wherein the control device comprises an indicator unit for the state of charge of the energy storage device.
6. Instrument as defined in claim 1, wherein the indicator unit for the state of charge comprises an indicator element for indicating when the state of charge has reached the predetermined state of residual charge or has fallen below the predetermined state of residual charge.
7. Surgical instrument, comprising:
an energy-driven operating device,
an energy storage device, and
a control device for supplying the operating device with energy from the energy storage device, wherein:
the operating device comprises a tool, the tool having an end or operating position and a rest position,
the control device supplies the operating device with energy as required for operating the tool,
when a state of charge of the energy storage device has either reached a predetermined state of a residual charge or has fallen below the predetermined state of the residual charge for a first time, the control device makes the residual charge available for returning the tool into the rest position,
the energy storage device comprises a first and a second storage element, and
when the state of charge of one of the storage elements reaches the predetermined state of residual charge or has fallen below the predetermined state of residual charge for the first time the other storage element is used to return the tool of the operating device from the end or operating position into the rest position.
8. Instrument as defined in claim 7, wherein:
the first storage element is used for transferring the tool of the operating device from the rest position into the end or operating position,
the second storage element is used for transferring the tool from the end or operating position into the rest position, and
an energy content of the second storage element is greater than approximately 105% of the energy required at the most for a required number of return movements.
9. Instrument as defined in claim 7, wherein the first and the second storage elements have the same charging capacity.
10. Instrument as defined in claim 7, wherein the first and the second storage elements are connected to form one unit.
11. Method for operating a surgical instrument, the surgical instrument comprising:
an energy-driven operating device which comprises a tool, the tool having an end or operating position and a rest position,
an energy storage device comprising a gas cartridge, and
a control device for supplying the operating device with energy from the energy storage device for operating the tool, the control device comprising a monitoring unit for detecting a state of charge of the energy storage device,
the method comprising:
monitoring the state of charge of the energy storage device during an operating processes of the tool by means of the monitoring unit to determine whether the state of charge of the energy storage device has reached a predetermined state of residual charge or has fallen below the predetermined state of residual charge for a first time, and
making the residual charge available for returning the tool of the operating device into the rest position when the state of charge of the energy storage device has reached the predetermined state of residual charge or has fallen below the predetermined state of residual charge for the first time,
wherein the monitoring unit comprises a pneumatically actuatable valve allowing activation of the tool of the operating device and, where applicable, a transfer of the tool of the operating device from the rest position into the end or operating position as long as the state of charge of the gas cartridge is above the predetermined state of residual charge.
12. Method as defined in claim 11, wherein:
the operating process comprises the transfer of the tool of the operating device from the rest position into the operating position and, where applicable, the end position as well as a return of the tool of the operating device from the operating or end position into the rest position, and
the operating process once begun will be completed and the tool of the operating device returned thereafter into the rest position when the state of charge of the energy storage device has reached the predetermined state of residual charge or has fallen below the predetermined state of residual charge for the first time.
13. Method as defined in claim 12, wherein when the state of charge of the energy storage device has reached the predetermined state of residual charge or has fallen below the predetermined state of residual charge for the first time a renewed activation of the operating device, resulting in a transfer of the tool of the operating device from the rest position into the operating or end position, is blocked.

14. Method as defined in claim 11, wherein the operating process once begun will be stopped and the tool of the operating device returned into the rest position when the state of charge of the energy storage device has reached the predetermined state of residual charge or has fallen below the predetermined state of residual charge for the first time.

15. Method as defined in claim 11, wherein an indicator unit is activated when the state of charge of the energy storage device has reached the predetermined state of residual charge or has fallen below the predetermined state of residual charge for the first time.

16. Instrument as defined in claim 7, wherein:
    the control device comprises a monitoring unit for detecting the state of charge of the energy storage device,
    the monitoring unit blocks any renewed activation of the tool of the operating device when the state of charge has reached the predetermined state of residual charge or has fallen below the predetermined state of residual charge for the first time.

17. Instrument as defined in claim 7, wherein the predetermined state of residual charge is adjustable.

18. Instrument as defined in claim 17, wherein the predetermined state of residual charge is adjustable such that the tool of the operating device is adapted to be transferred from the end or operating position into the rest position after the activation of the tool has been blocked.

19. Instrument as defined in claim 17, wherein the control device comprises an indicator unit for the state of charge of the energy storage device.

20. Instrument as defined in claim 17, wherein the indicator unit for the state of charge comprises an indicator element for indicating when the state of charge has reached the predetermined state of residual charge or has fallen below the predetermined state of residual charge for the first time.

21. Method for operating a surgical instrument, the surgical instrument comprising:
    an energy-driven operating device which comprises a tool, the tool having an end or operating position and a rest position,
    an energy storage device comprising a first and a second storage element, and
    a control device for supplying the operating device with energy from the energy storage device for operating the tool,
    the method comprising:
        monitoring a state of charge of the energy storage device during an operating processes of the tool to determine whether the state of charge of the first or the second storage element has reached a predetermined state of residual charge or has fallen below the predetermined state of residual charge for a first time, and
        when a state of charge of one of the storage elements has one of reached the predetermined state of a residual charge or has fallen below the predetermined state of residual charge for the first time, using the other storage element to return the tool of the operating device from the end or operating position into the rest position.

22. Method as defined in claim 21, wherein:
    the first storage element is used for transferring the tool of the operating device from the rest position into the end or operating position,
    the second storage element is used for transferring the tool from the end or operating position into the rest position, and
    an energy content of the second storage element is greater than approximately 105% of the energy required at the most for a required number of return movements.

23. Method as defined in claim 21, wherein the first and the second storage elements have the same charging capacity.

24. Method as defined in claim 21, wherein the first and the second storage elements are connected to form one unit.

* * * * *